(12) United States Patent
Sano et al.

(10) Patent No.: US 7,781,074 B2
(45) Date of Patent: Aug. 24, 2010

(54) ORGANIC ELECTROLUMINESCENT ELEMENT

(75) Inventors: Satoshi Sano, Kanagawa (JP); Tatsuya Igarashi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 1202 days.

(21) Appl. No.: 11/372,272

(22) Filed: Mar. 10, 2006

(65) Prior Publication Data

US 2006/0210831 A1   Sep. 21, 2006

(30) Foreign Application Priority Data

Mar. 16, 2005   (JP)   ............................. 2005-075769

(51) Int. Cl.
*H01L 51/54* (2006.01)
*C09K 11/06* (2006.01)

(52) U.S. Cl. ...................... 428/690; 428/917; 313/504; 257/E51.044; 546/4

(58) Field of Classification Search ....................... None
See application file for complete search history.

(56) References Cited

U.S. PATENT DOCUMENTS

| | | | |
|---|---|---|---|
| 6,303,238 B1 | 10/2001 | Thompson et al. | |
| 6,653,654 B1 | 11/2003 | Che | |
| 2006/0060842 A1* | 3/2006 | Sano et al. | 257/40 |
| 2006/0073359 A1* | 4/2006 | Ise et al. | 428/690 |
| 2006/0134461 A1* | 6/2006 | Huo et al. | 428/690 |
| 2006/0202197 A1* | 9/2006 | Nakayama et al. | 257/40 |

OTHER PUBLICATIONS

Brenda Ka-Wen Chiu et al., Synthesis, characterization and spectroscopic studies of cyclometalated platinum(II) complexes containing *meta*-bis(2-pyridoxy)benzene, Journal of Organometallic Chemistry, 689, 2004, 2888-2899.

* cited by examiner

*Primary Examiner*—Marie R. Yamnitzky
(74) *Attorney, Agent, or Firm*—Birch, Stewart, Kolasch & Birch, LLP

(57) ABSTRACT

An organic electroluminescent element comprising a pair of electrodes and at least one organic compound layer including a luminescent layer between the pair of electrodes, wherein at least one of the at least one organic compound layer comprises a compound represented by the following formula (I):

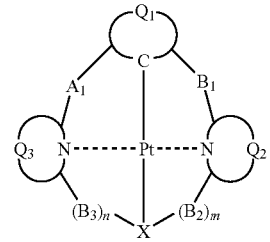

Formula (I)

wherein in formula (I), $Q_1$ represents an atomic group necessary for forming an unsaturated ring together with the carbon atom; $Q_2$ and $Q_3$ each independently represent an atomic group necessary for forming an unsaturated ring together with the nitrogen atom; X represents a partial structure comprising an atom that is linked to the platinum atom; $A_1$ represents a linking group; $B_1$, $B_2$ and $B_3$ each independently represent a linking group or a single bond; m and n each independently represent 0 or 1; and at least one of m and n is not 1.

5 Claims, No Drawings

ORGANIC ELECTROLUMINESCENT ELEMENT

CROSS-REFERENCE TO RELATED APPLICATION

This application claims priority under 35 USC 119 from Japanese patent Application No. 2005-075769, the disclosure of which is incorporated by reference herein.

BACKGROUND OF THE INVENTION

1. Field of the Invention

The present invention relates to a platinum complex and an organic electroluminescent element (hereinafter, occasionally referred to also as "element" for short).

2. Description of Related Art

In the development of an organic electroluminescent element of recent years, studies on the improvement of external quantum efficiency have been conducted. Among such elements, an element containing a phosphorescence-emitting material comprising heavy metals such as iridium and platinum has attained high efficiency and attracted attention.

In the development of a luminescent material using platinum, an example in which an aryl group is linked by an ether linkage is described (for example, in Journal of Organometallic Chemistry, Vol. 689, pp. 2888 to 2899 (2004)). Such platinum complex is characterized by realizing a shorter luminescent wavelength than that of a quadridentate platinum complex such as an octaethylporphine platinum complex which has been reported (for example, in U.S. Pat. Nos. 6,303,238 B1 and 6,653,654 B1).

However, there is a problem in that the luminescence of the platinum complex described in Journal of Organometallic Chemistry, Vol. 689, pp. 2888 to 2899 (2004) is very weak at room temperature. Further, when a luminescent material contains remaining unidentate ligands, (particularly when a halogen atom such as a chlorine atom is used), the element using the luminescent material has low durability and improvements thereof have been needed.

SUMMARY OF THE INVENTION

Under these circumstances, the present inventors have conducted intensive study and made the present invention.

The invention provides an organic electroluminescent element comprising a pair of electrodes and at least one organic compound layer including a luminescent layer between the pair of electrodes. At least one of the at least one organic compound layer comprises a compound represented by the following formula (I):

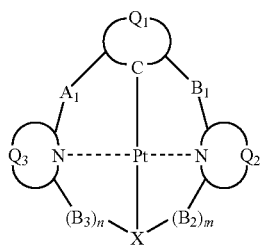

Formula (I)

In formula (I), $Q_1$ represents an atomic group necessary for forming an unsaturated ring together with the carbon atom. $Q_2$ and $Q_3$ each independently represent an atomic group necessary for forming an unsaturated ring together with the nitrogen atom. X represents a partial structure containing an atom that is linked to a platinum atom. $A_1$ represents a linking group. $B_1$, $B_2$ and $B_3$ each independently represent a linking group or a single bond. When X represents a substituted or non-substituted aryl group, at least one of $B_1$ and $B_3$ is not a single bond. In formula (I), m and n each independently represent 0 or 1; however, at least one of m and n is not 1. When m represents 0, the unsaturated ring formed by $Q_2$ and the nitrogen atom is not linked to X. When n represents 0, the unsaturated ring formed by $Q_3$ and the nitrogen atom is not linked to X.

The compound of formula (I) may be a compound represented by formula (II):

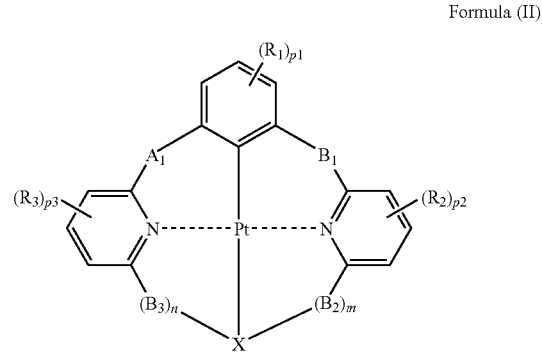

Formula (II)

In formula (II), $R_1$, $R_2$ and $R_3$ each independently represent a substituent; $p_1$, $p_2$ and $p_3$ each independently represent an integer of 0 to 3; and $A_1$, $B_1$, $B_2$, $B_3$, m, n and X have the same definitions as $A_1$, $B_1$, $B_2$, $B_3$, m, n and X in formula (I), respectively.

The compound of formula (I) may be a compound represented by the following formula (III):

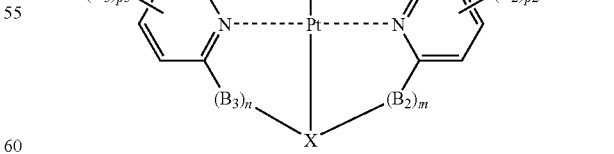

Formula (III)

In formula (III), the definitions of $R_1$, $R_2$, $R_3$, $p_1$, $p_2$ and $p_3$ are the same as $R_1$, $R_2$, $R_3$, $p_1$, $p_2$ and $p_3$ in formula (II), respectively; and the definitions of $A_1$, $B_2$, $B_3$, m, n and X are the same as $A_1$, $B_2$, $B_3$, m, n and X in formula (I), respectively.

The compound of formula (I) may be a compound represented by the following formula (IV):

Formula (IV)

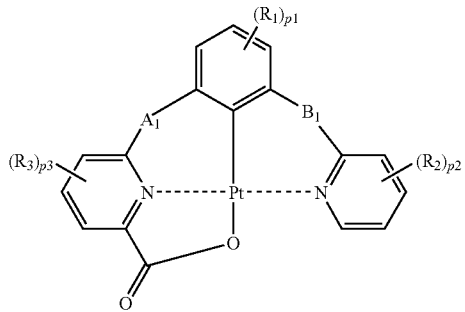

In formula (IV), $A_1$ and $B_1$ have the same definitions as $A_1$ and $B_1$ in formula (I), respectively; and $R_1$, $R_2$, $R_3$, $p_1$, $p_2$ and $p_3$ have the same definitions as $R_1$, $R_2$, $R_3$, $p_1$, $p_2$ and $p_3$ in formula (II), respectively.

The compound of formula (I) may be a compound represented by the following formula (V):

Formula (V)

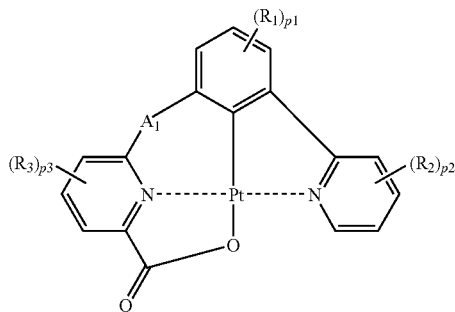

In formula (V), $A_1$ has the same definition as that of $A_1$ in formula (I); the definitions of $R_1$, $R_2$, $R_3$, $p_1$, $p_2$ and $p_3$ are the same as $R_1$, $R_2$, $R_3$, $p_1$, $p_2$ and $p_3$ in formula (II), respectively.

The compound of formula (I) may be a compound represented by the following formula (VI):

Formula (VI)

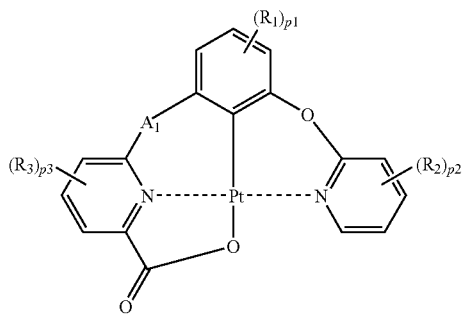

In formula (VI), $A_1$ has the same definition as that of $A_1$ in formula (I) and $R_1$, $R_2$, $R_3$, $p_1$, $p_2$ and $p_3$ have the same definitions as $R_1$, $R_2$, $R_3$, $p_1$, $p_2$ and $p_3$ in formula (II), respectively.

According to the invention, platinum complexes having favorable luminescent characteristics (including luminance, quantum yield, and driving voltage), durability and vapor deposition property are provided, and luminescent elements containing the platinum complexes are also provided.

DETAILED DESCRIPTION OF THE INVENTION

An organic electroluminescent element according to the present invention comprises a pair of electrodes and at least one organic compound layer including a luminescent layer between the pair of electrodes, wherein at least one of the at least one organic layer comprises a compound represented by formula (I) (hereinafter, occasionally referred to also as "compound of the invention").

Owing to the constitution described above, namely, owing to the presence of the compound of the invention with superior luminescent characteristics (including luminance, quantum yield and driving voltage), durability and vapor-depositability in the organic compound layer, the organic electroluminescent element has an excellent luminescent characteristics (including luminance, quantum yield and driving voltage), durability and a vapor depositability.

Hereinafter, the compound represented by formula (I) will be described.

In formula (I), $Q_1$ represents an atomic group necessary for forming an unsaturated ring together with the carbon atom. $Q_2$ and $Q_3$ each independently represent an atomic group necessary for forming an unsaturated ring together with the nitrogen atom.

The above-described atomic groups are not particularly limited and each may be independently selected from atomic groups consisting of atoms selected from carbon, nitrogen, silicon, sulfur, oxygen, germanium and phosphorus atoms. Each link between atoms in the unsaturated ring may be a single bond, a double bond, or a triple bond so long as at least one unsaturated bond is contained in the ring.

$Q_1$, $Q_2$ and $Q_3$ each may independently represent an atomic group consisting of atoms selected preferably from carbon, nitrogen, silicon, sulfur and oxygen atoms, more preferably from carbon, nitrogen and silicon atoms, still more preferably from carbon and nitrogen atoms. In a particularly preferable embodiment, $Q_1$, $Q_2$ and $Q_3$ each independently represent an atomic group consisting of carbon atoms, and the unsaturated ring formed by $Q_1$ and the carbon atom is a substituted benzene ring, and the unsaturated ring formed by $Q_2$ and the nitrogen atom and the unsaturated ring formed by $Q_3$ and the nitrogen atom are each independently a substituted pyridine ring.

If possible, the atomic groups of $Q_1$, $Q_2$ and $Q_3$ each may have a substituent, and the substituents on the respective atomic groups may be the same as or different from one another.

Examples of the substituents include an alkyl group (having preferably 1 to 30 carbon atoms, more preferably 1 to 20 carbon atoms and particularly preferably 1 to 10 carbon atoms, such as methyl, ethyl, isopropyl, tert-butyl, n-octyl, n-decyl or n-hexadecyl); a cycloalkyl group (having preferably 3 to 30 carbon atoms, more preferably 3 to 20 carbon atoms and particularly preferably 3 to 10 carbon atoms, such as cyclopropyl, cyclopenthyl or cyclohexyl); an alkenyl group (having preferably 2 to 30 carbon atoms, more preferably 2 to 20 carbon atoms and particularly preferably 2 to 10 carbon atoms, such as vinyl, allyl, 2-butenyl or 3-pentenyl); an alkynyl group (having preferably 2 to 30 carbon atoms, more preferably 2 to 20 carbon atoms and particularly preferably 2 to 10 carbon atoms, such as propargyl or 3-pentenyl);

an aryl group (having preferably 6 to 30 carbon atoms, more preferably 6 to 20 carbon atoms and particularly preferably 6 to 12 carbon atoms, such as phenyl, p-methylphenyl, naphthyl or anthranyl); an amino group (having preferably 0 to 30 carbon atoms, more preferably 0 to 20 carbon atoms and particularly preferably 0 to 10 carbon atoms, such as amino, methylamino, dimethylamino, diethylamino, dibenzylamino, diphenylamino or ditolylamino); an alkoxy group (having preferably 1 to 30 carbon atoms, more preferably 1 to 20 carbon atoms and particularly preferably 1 to 10 carbon atoms, such as methoxy, ethoxy, butoxy or 2-ethylhexyloxy); an aryloxy group (having preferably 6 to 30 carbon atoms, more preferably 6 to 20 carbon atoms and particularly preferably 6 to 12 carbon atoms, such as phenyloxy, 1-naphthyloxy or 2-naphthyloxy); a heterocyclic oxy group (having preferably 1 to 30 carbon atoms, more preferably 1 to 20 carbon atoms and still more preferably 1 to 12 carbon atoms, such as pyridyloxy, pyradyloxy, pyrimidyloxy or quinolyloxy); an acyl group (having preferably 1 to 30 carbon atoms, more preferably 1 to 20 carbon atoms and particularly preferably 1 to 12 carbon atoms, such as acetyl, benzoyl, formyl or pivaloyl); an alkoxy carbonyl group (having preferably 2 to 30 carbon atoms, more preferably 2 to 20 carbon atoms and particularly preferably 2 to 12 carbon atoms, such as methoxycarbonyl or ethoxycarbonyl); an aryloxycarbonyl group (having preferably 7 to 30 carbon atoms, more preferably 7 to 20 carbon atoms and particularly preferably 7 to 12 carbon atoms, such as phenyloxycarbonyl); an acyloxy group (having preferably 2 to 30 carbon atoms, more preferably 1 to 20 carbon atoms and particularly preferably 1 to 10 carbon atoms, such as acetoxy or benzoyloxy); an acylamino group (having preferably 1 to 30 carbon atoms, more preferably 1 to 20 carbon atoms and particularly preferably 1 to 10 carbon atoms, such as acetylamino or benzoylamino); an alkoxycarbonylamino group (having preferably 2 to 30 carbon atoms, more preferably 2 to 20 carbon atoms and particularly preferably 2 to 12 carbon atoms, such as methoxycarbonylamino); an aryloxycarbonylamino group (having preferably 7 to 30 carbon atoms, more preferably 7 to 20 carbon atoms and particularly preferably 7 to 12 carbon atoms, such as phenyloxycarbonylamino); a sulfonylamino group (having preferably 1 to 30 carbon atoms, more preferably 1 to 20 carbon atoms and particularly preferably 1 to 12 carbon atoms, such as methane sulfonylamino or benzene sulfonylamino); a sulfamoyl group (having preferably 0 to 30 carbon atoms, more preferably 0 to 20 carbon atoms and particularly preferably 0 to 12 carbon atoms, such as sulfamoyl, methylsulfamoyl, dimethylsulfamoyl or phenylsulfamoyl); a carbamoyl group (having preferably 1 to 30 carbon atoms, more preferably 1 to 20 carbon atoms and particularly preferably 1 to 12 carbon atoms, such as carbamoyl, methylcarbamoyl, diethylcarbamoyl or phenylcarbamoyl); an alkylthio group (having preferably 1 to 30 carbon atoms, more preferably 1 to 20 carbon atoms and particularly preferably 1 to 12 carbon atoms, such as methylthio or ethylthio); an arylthio group (having preferably 6 to 30 carbon atoms, more preferably 6 to 20 carbon atoms and particularly preferably 6 to 12 carbon atoms, such as phenylthio); a heterocyclic thio group (having preferably 1 to 30 carbon atoms, more preferably 1 to 20 carbon atoms and particularly preferably 1 to 12 carbon atoms, such as pyridylthio, 2-benzimidazolylthio, 2-benzoxazolylthio or 2-benzothiazolylthio); a sulfonyl group (having preferably 1 to 30 carbon atoms, more preferably 1 to 20 carbon atoms and particularly preferably 1 to 12 carbon atoms, such as mesyl or tosyl); a sulfinyl group (having preferably 1 to 30 carbon atoms, more preferably 1 to 20 carbon atoms and particularly preferably 1 to 12 carbon atoms, such as methane sulfinyl or benzene sulfinyl); a ureido group (having preferably 1 to 30 carbon atoms, more preferably 1 to 20 carbon atoms and particularly preferably 1 to 12 carbon atoms, such as ureido, methylureido or phenylureido); a phosphoric acid amido group (having preferably 1 to 30 carbon atoms, more preferably 1 to 20 carbon atoms and particularly preferably 1 to 12 carbon atoms, such as diethyl phosphoric acid amide or phenylphosphoric acid amide); a hydroxyl group; a mercapto group; a halogen atom (such as a fluorine atom, a chlorine atom, a bromine atom or an iodine atom, preferably a fluorine atom); a cyano group; a sulfo group; a carboxyl group; a nitro group; a hydroxamic acid group; a sulfino group; a hydrazino group; an imino group; a heterocyclic group (having preferably 1 to 30 carbon atoms and more preferably 1 to 12 carbon atoms, and containing, as a hetero atom, a nitrogen atom, an oxygen atom or a sulfur atom, such as imidazolyl, pyridyl, quinolyl, furyl, thienyl, piperidyl, morpholino, benzoxazolyl, benzimidazolyl, benzthiazolyl, a carbazolyl group or an azepinyl group); a silyl group (having preferably 3 to 40 carbon atoms, more preferably 3 to 30 carbon atoms and particularly preferably 3 to 24 carbon atoms, such as trimethylsilyl or triphenylsilyl); and a silyloxy group (having preferably 3 to 40 carbon atoms, more preferably 3 to 30 carbon atoms and particularly preferably 3 to 24 carbon atoms, such as trimethylsilyloxy or triphenylsilyloxy. These substituents may further be substituted.

In formula (I), $A_1$ represents a linking group. The linking group is not particularly limited and particularly preferably comprises at least one atom selected from carbon atoms, nitrogen atoms, oxygen atoms, sulfur atoms, silicon atoms, germanium atoms and phosphorus atoms, and a group selected from the following linking group collection (I) is particularly preferable:

Linking Group Collection (I)

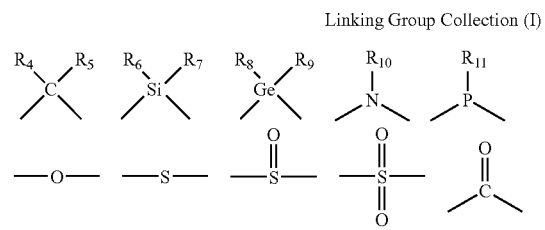

Linking Group Collection (I)

Next, the above-described linking group collection (I) will be described in detail.

In the above-described linking group collection (I), $R_4$, $R_5$, $R_6$, $R_7$, $R_8$, $R_9$, $R_{10}$ and $R_{11}$ each independently represent a hydrogen atom or a substituent. When any of $R_4$, $R_5$, $R_6$, $R_7$, $R_8$, $R_9$, $R_{10}$ and $R_{11}$ represents a substituent, the substituent may be selected from the above-described examples of the substituents on the atomic groups represented by $Q_1$, $Q_2$ and $Q_3$ in the unsaturated rings. $R_4$, $R_5$, $R_6$, $R_7$, $R_8$, $R_9$, $R_{10}$ and $R_{11}$ each may have a substituent if substitutable. $R_4$, $R_5$, $R_6$, $R_7$, $R_8$, $R_9$, $R_{10}$ and $R_{11}$ each may be bonded to the atomic group represented by $Q_1$, $Q_2$ or $Q_3$ to form a ring. $R_4$ and $R_5$ may be bonded to each other to form a ring. $R_6$ and $R_7$ may be bonded to each other to form a ring. $R_8$ and $R_9$ may be may be bonded to each other to form a ring.

The linking group represented by $A_1$ is preferably selected from the linking group collection (I), more preferably from —C($R_4$)($R_5$)—, —Si($R_6$)($R_7$)—, —N($R_{10}$)—, —O—, —S— and —CO—, still more preferably from —C($R_4$)

$(R_5)$—, —$Si(R_6)(R_7)$—, —O— and —S— and, furthermore preferably from —$C(R_4)(R_5)$— and —O—.

When $A_1$ represents —$C(R_4)(R_5)$—, $R_4$ and $R_5$ each preferably represent an alkyl group, a cycloalkyl group, an aryl group, a halogen atom, an amino group, an alkylthio group, an arylthio group, an alkyloxy group, an aryloxy group, a hydroxyl goup, a mercapto group or a halogen atom. These groups are preferably selected from the above-described preferable examples of the substituents on $Q_1$ to $Q_3$. $R_4$ and $R_5$ are each still more preferably an alkyl group, a cycloalkyl group, an aryl group, a halogen atom, an alkylthio group, an arylthio group, an alkyloxy group, an aryloxy group or a halogen atom and, further more preferably an alkyl group or an aryl group. These substituents each may have a substituent if substitutable.

When $A_1$ represents —$Si(R_6)(R_7)$—, $R_6$ and $R_7$ each independently preferably represent an alkyl group, a cycloalkyl group, an aryl group, a halogen atom, an amino group, an alkylthio group, an arylthio group, an alkyloxy group, an aryloxy group, a hydroxyl goup, a mercapto group or a halogen atom. These groups are preferably selected from the above-described preferable examples of the substituents on $Q_1$ to $Q_3$. $R_6$ and $R_7$ are each still more preferably an alkyl group, a cycloalkyl group, an aryl group, a halogen atom, an alkylthio group, an arylthio group, an alkyloxy group, an aryloxy group or a halogen atom, and further more preferably an alkyl group or an aryl group. These substituents each may have a substituent if substitutable.

When $A_1$ represents —$N(R_{10})$—, $R_{10}$ preferably represents an alkyl group, a cycloalkyl group or an aryl group. These groups are preferably selected from the above-described preferable examples of the substituents on $Q_1$ to $Q_3$. $R_{10}$ is more preferably an alkyl group or an aryl group, and still more preferably an aryl group. These substituents each may have a substituent if substitutable.

In formula (I), $B_1$, $B_2$ and $B_3$ each independently represent a linking group or a single bond. When X represents a substituted or non-substituted aryl group, at least one of $B_1$ and $B_3$ is different from a single bond.

$B_1$ represents preferably a group selected from the linking group collection (I) and a single bond, more preferably from —$C(R_4)(R_5)$—, —$N(R_{10})$—, —O—, —S—, —CO— and a single bond, and still more preferably from —O— and a single bond.

When $B_1$ represents —$C(R_4)(R_5)$—, —$Si(R_6)(R_7)$— or —$N(R_{10})$—, preferable examples thereof are the same as those of —$C(R_4)(R_5)$—, —$Si(R_6)(R_7)$— and —$N(R_{10})$— described in the explanation about $A_1$, respectively.

$B_2$ and $B_3$ each independently represent preferably a group selected from the linking group collection (I) and a single bond, and more preferably from —$C(R_4)(R_5)$—, —O—, —S—, —SO—, —$SO_2$—, —CO— and a single bond, and still more preferably from —O—, —CO— and a single bond.

When any of $B_2$ and $B_3$ represents —$C(R_4)(R_5)$—, —$Si(R_6)(R_7)$— or —$N(R_{10})$—, preferable examples thereof are the same as those of —$C(R_4)(R_5)$—, —$Si(R_6)(R_7)$— and —$N(R_{10})$— described in the explanation about $A_1$, respectively.

In formula (I), m and n each independently represent an integer of 0 or 1. However, at least one of m and n represents 0, and the compound represented by formula (I) is not a complete cyclic compound having platinum in the center. When m represents 0, X is not bonded to the unsaturated ring formed by $Q_2$ and the nitrogen atom. When n represents 0, X is not bonded to the unsaturated ring formed by $Q_3$ and the nitrogen atom. In a preferable embodiment, one of m and n represents 1.

X represents a partial structure containing an atom that is bonded to the platinum atom.

The partial structure represented by X is preferably a group having a carbon atom that is bonded to the platinum atom, a group having a nitrogen atom that is bonded to the platinum atom, a group having a silicon atom that is bonded to the platinum atom, a group having a phosphorus atom that is bonded to the platinum atom, a group having an oxygen atom that is bonded to the platinum atom or a group having a sulfur atom that is bonded to the platinum atom, more preferably a group having a carbon, nitrogen, oxygen, or sulfur atom bonded to the platinum atom, still more preferably a group having a sulfur, nitrogen, or oxygen atom bonded to the platinum atom, and particularly preferably a group having an oxygen atom bonded to the platinum atom.

The group having a carbon atom that is bonded to the platinum atom is preferably a substituted or non-substituted aryl group having a carbon atom that is bonded to the platinum atom, a substituted or non-substituted 5-membered heteroaryl group having a carbon atom that is bonded to the platinum atom, or a substituted or non-substituted 6-membered heteroaryl group having a carbon atom that is bonded to the platinum atom, and particularly preferably a substituted aryl group having a carbon atom that is bonded to the platinum atom.

The group having an oxygen atom that is bonded to the platinum atom is preferably a substituted or non-substituted hydroxyl group or a substituted or non-substituted carboxyl group, and more preferably a substituted or non-substituted carboxyl group.

The group having a nitrogen atom that is bonded to the platinum atom is preferably a substituted amino group or a nitrogen-containing 5-membered heteroaryl group having a nitrogen atom that is bonded to the platinum atom, more preferably a nitrogen-containing 5-membered heteroaryl group having a nitrogen atom that is bonded to the platinum atom, and particularly preferably a substituted carbazole, a substituted pyrrole, a substituted indole or the like.

The group having a phosphorus atom that is bonded to the platinum atom is preferably a substituted phosphino group. The group having a silicon atom that is bonded to the platinum atom is preferably a substituted silyl group. The group having a sulfur atom that is bonded to the platinum atom is preferably a thiol group or a substituted thiol group.

Next, a preferable range of formula (I) is described.

In a preferable embodiment, the unsaturated ring formed by $Q_1$ and the carbon atom is preferably a 6-membered ring, and the unsaturated ring formed by the nitrogen atom and $Q_2$ and the unsaturated ring formed by the nitrogen atom and $Q_3$ are each a 6-membered ring. In another preferable embodiment, the unsaturated ring formed by $Q_1$ and the carbon atom is a 6-membered ring, and the unsaturated ring formed by the nitrogen atom and $Q_2$ and the unsaturated ring formed by the nitrogen atom and $Q_3$ are each a 5-membered ring.

Next, a more preferable range of formula (I) is described.

The compound represented by formula (I) is more preferably a compound represented by formula (II) or formula (III).

Formula (II) is described below in detail.

In formula (II), $R_1$, $R_2$ and $R_3$ each independently represent a substituent. The substituent may be selected from the above-described examples of the substituent on the unsaturated ring containing $Q_1$, $Q_2$, or $Q_3$. If substitutable, $R_1$, $R_2$ and $R_3$ may each may have a substituent.

Preferable examples of $R_1$ include an alkyl group, a cycloalkyl group, an aryl group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxyl group, a mercapto group, a halogen atom, a cyano group, a sulfo group, a carboxyl group, a nitro group, a sulfino group, a heterocyclic group, and a silyl group. Preferable examples of these groups are the same as those of the above-described examples of the substituent on $Q_1$, $Q_2$, or $Q_3$. $R_1$ is more preferably an alkyl group, an aryl group, a sulfonyl group, a halogen atom, a cyano group, a nitro group, or a heterocyclic group, and still more preferably an alkyl group, an aryl group, a halogen atom, or a cyano group. If substitutable, these groups may have a substituent.

Preferable examples of $R_2$ and $R_3$ include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxyl group, a mercapto group, a halogen atom, a cyano group, a sulfo group, a carboxyl group, a nitro group, a sulfino group, a heterocyclic group, and a silyl group. Preferable examples of these groups are the same as those of the above-described examples of the substituent on $Q_1$, $Q_2$, or $Q_3$. $R_2$ and $R_3$ are each more preferably an alkyl group, a cycloalkyl group, an amino group, an aryl group, a heterocyclic group, an alkoxy group, or an aryloxy group, still more preferably an alkyl group, an alkoxy group, or an amino group. If substitutable, these groups may have a substituent.

Further, $p_1$, $p_2$ and $p_3$ each independently represent an integer of 0 to 3. When $p_1$ represents 2 or greater, there are plural $R_1$'s, and they may be the same as or different from each other, and they may combine with each other to form a ring. When $p_2$ represents 2 or greater, there are plural $R_2$'s, and they may be the same as or different from each other, and they may combine with each other to form a ring. When $p_3$ represents 2 or greater, there are plural $R_3$'s, and they may be the same as or different from each other, and they may combine with each other to form a ring. Further, $R_1$ and $R_2$ may combine each other to form a ring. $R_1$ and $R_3$ may combine each other to form a ring. $R_2$ and $R_3$ may combine each other to form a ring. In formula (II), $p_1$, $p_2$ and $p_3$ each independently represent an integer of preferably 0 to 2, and more preferably 0 or 1.

The above-described $A_1$, $B_1$, $B_2$, $B_3$, m, n and X have the same definitions as in formula (I). Preferable examples thereof are the same as in the case of formula (I).

Next, formula (III) is described.

In formula (III), $A_1$, $B_2$, $B_3$, m, n and X have the same definitions as in formula (I). Preferable examples thereof are also the same as in the case of formula (I). $R_1$, $R_2$, $R_3$, $p_1$, $p_2$ and $p_3$ have the same definitions as in formula (II). Preferable examples thereof are also the same as in the case of formula (II).

Next, more preferable range of formula (I) is described.

The compound represented by formula (I) is more preferably a compound represented by the following formula (IV) or (V):

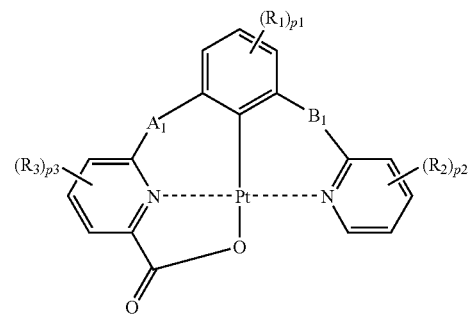

Formula (IV)

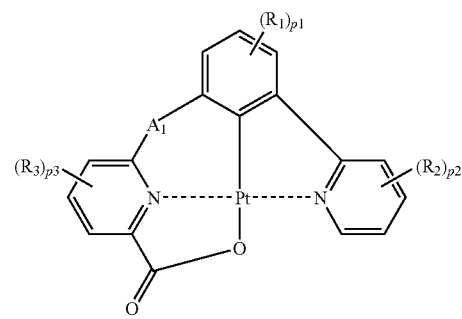

Formula (V)

Next, formula (IV) is described.

In formula (IV), $A_1$ and $B_1$ have the same definitions as those of $A_1$ and $B_1$ in formula (I), respectively. Preferable examples thereof are also the same as in the case of formula (I). $R_1$, $R_2$, $R_3$, $p_1$, $p_2$ and $p_3$ have the same definitions as in formula (II). Preferable examples thereof are also the same as in the case of formula (II).

Next, formula (V) is described.

In formula (V), $A_1$ has the same definition as $A_1$ in formula (I). Preferable examples thereof are also the same as in formula (I). $R_1$, $R_2$, $R_3$, $p_1$, $p_2$ and $p_3$ have the same definitions as in formula (II). Preferable examples thereof are also the same as in the case of formula (II).

The compound represented by formula (I) according to the invention may be a low molecular compound or may be an oligomer compound or a polymer compound (whose weight-average molecular weight (in terms of polystyrene conversion) is preferably 1000 to 5000000, more preferably 2000 to 1000000, and still more preferably 3000 to 100000). In the case of the polymer compound, the structure of formula (I) may be contained in the polymer main chain or may be contained in a side chain of the polymer. When the compound represented by formula (I) is a polymer compound, the polymer compound may be a homopolymer compound or a copolymer. The compound represented by formula (I) according to the invention is preferably a low molecular compound.

The compound represented by formula (I) according to the invention is applicable to an organic EL element and is capable of being used in any of an electron transporting material, a hole blocking material, an electron blocking material and an exciton blocking material. The compound represented by formula (I) is preferably used in a hole injecting material, a hole transport material, an electron blocking material or a luminescent material, more preferably in a hole injecting material or in a luminescent material, and still more preferably in a luminescent material. When the compound is used as a luminescent material, such luminescence may be ultraviolet emission, visible-light emission, infrared emission, or the like, and may be fluorescence emission or phosphorescence emission.
Next, specific examples of the compounds of the invention will be shown below, but the examples should not be construed as limiting the invention.
(1)
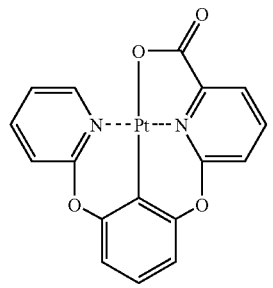
(2)
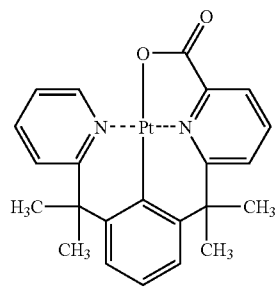
(3)
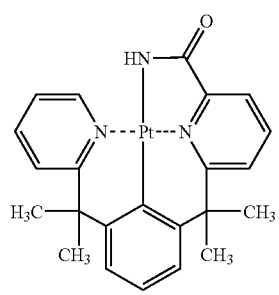
(4)
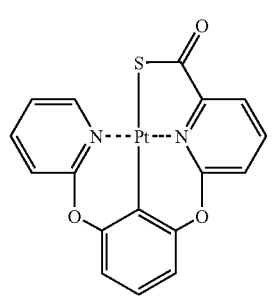
(5)
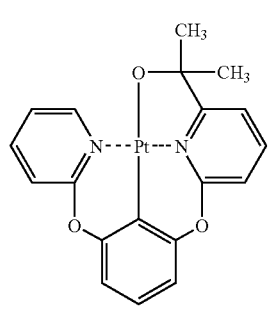
-continued
(6)
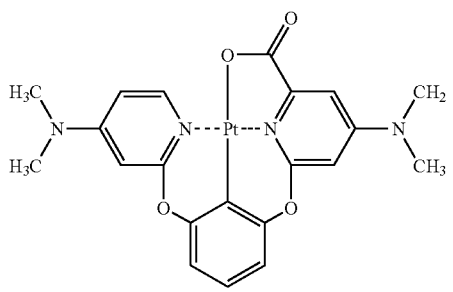
(7)
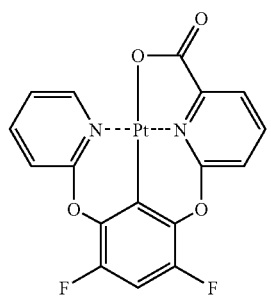
(8)
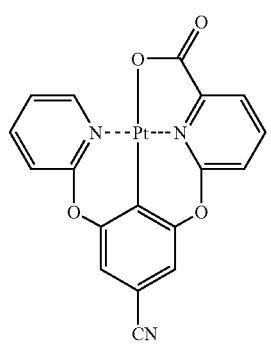
(9)
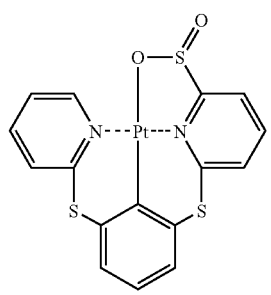
(10)
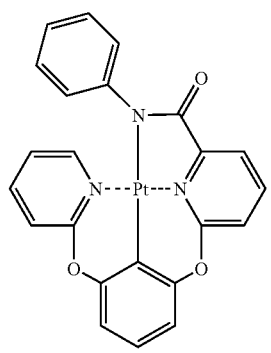

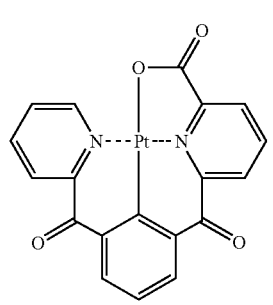
(11)
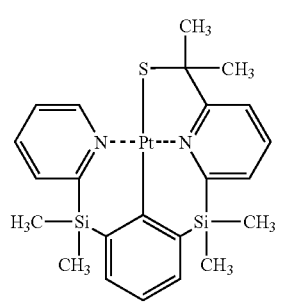
(12)
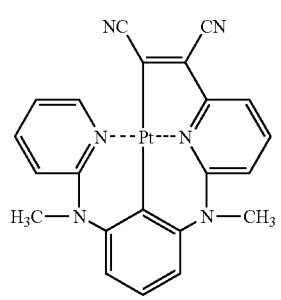
(13)
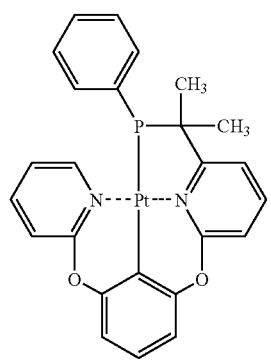
(14)
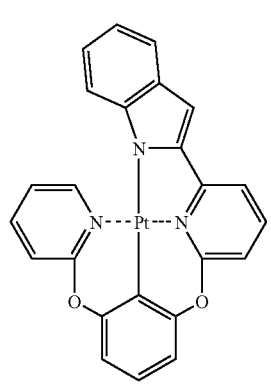
(15)
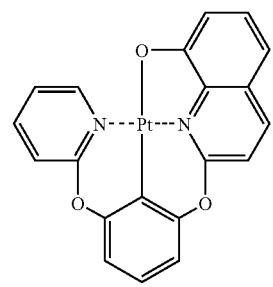
(16)
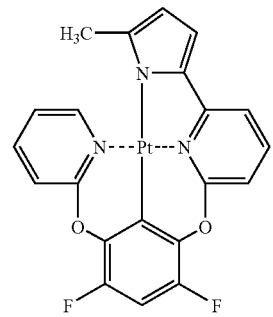
(17)
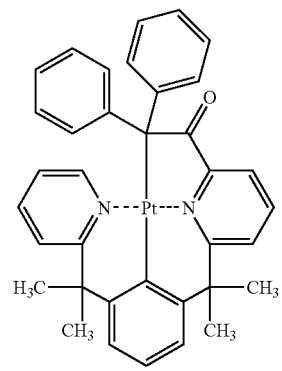
(18)
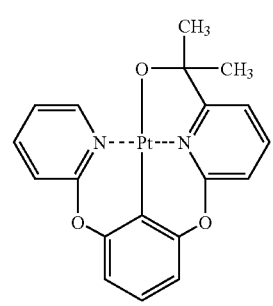
(19)
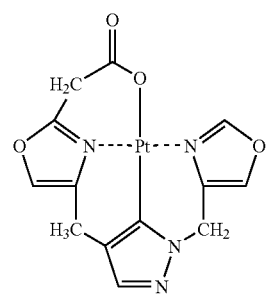
(20)

(21) 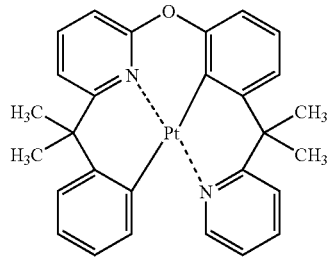
(22) 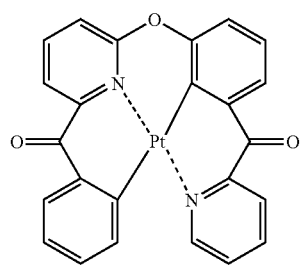
(23) 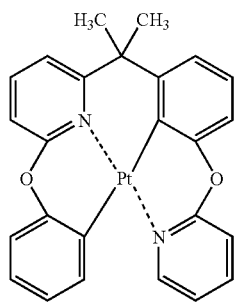
(24) 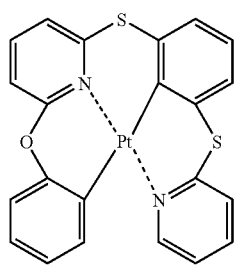
(25) 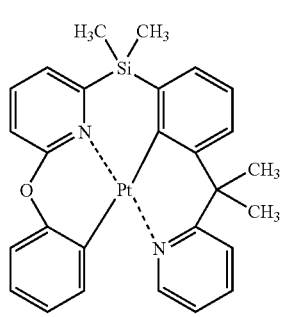
(26) 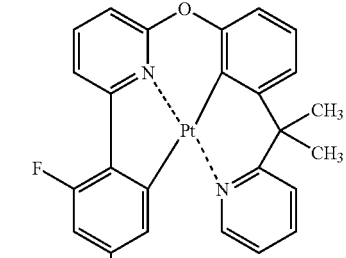
(27) 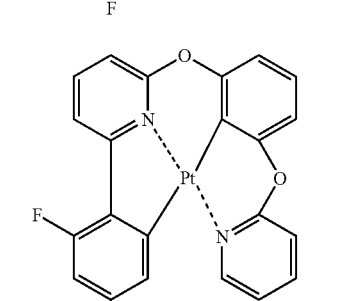
(28) 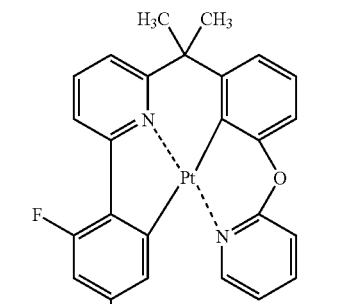
(29) 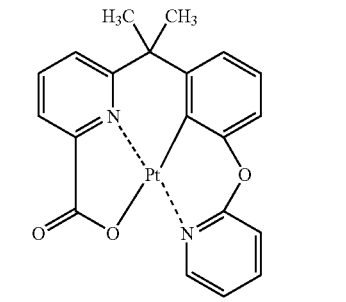
(30) 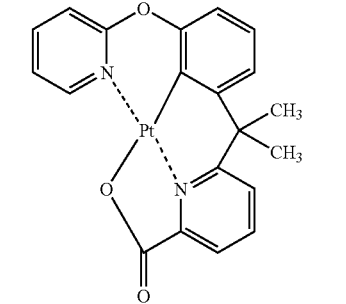

-continued
(31) 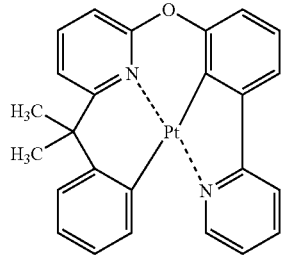
(32) 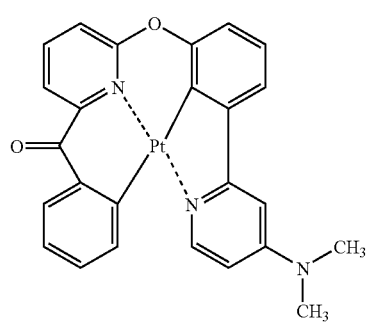
(33) 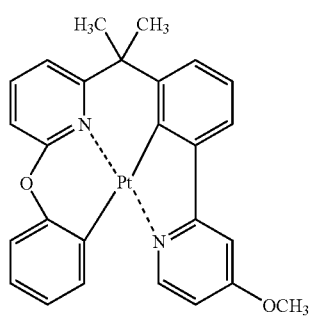
(34) 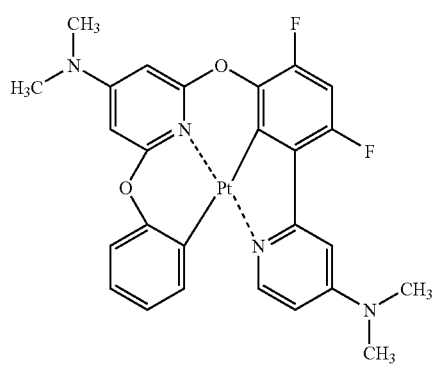
(35) 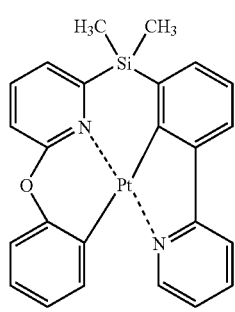
-continued
(36) 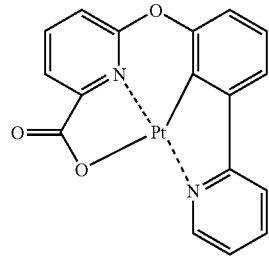
(37) 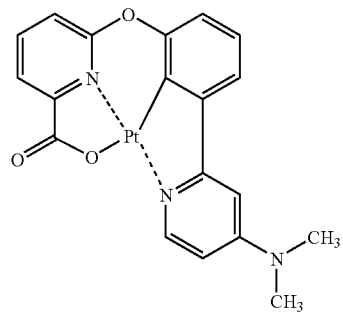
(38) 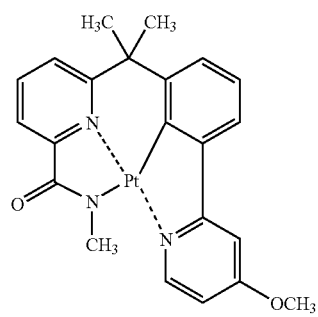
(39) 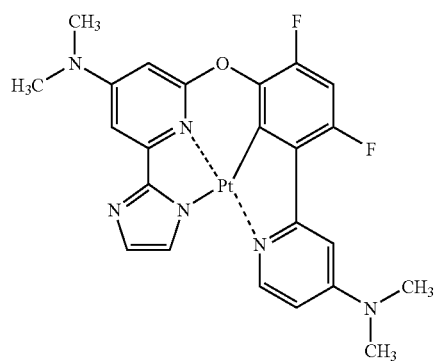
(40) 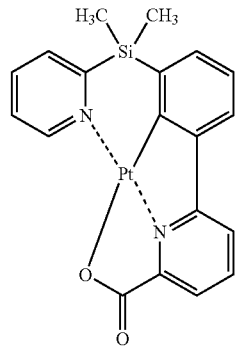

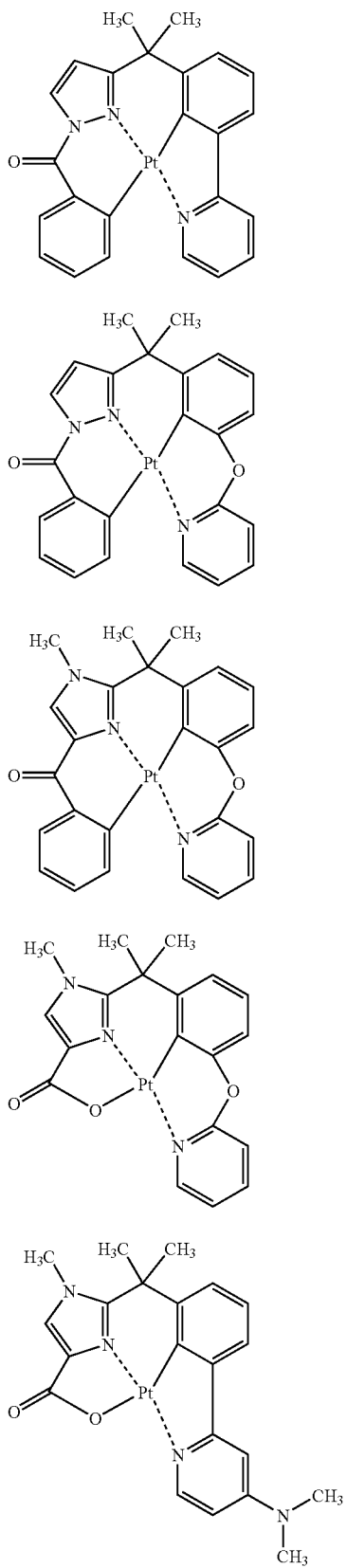
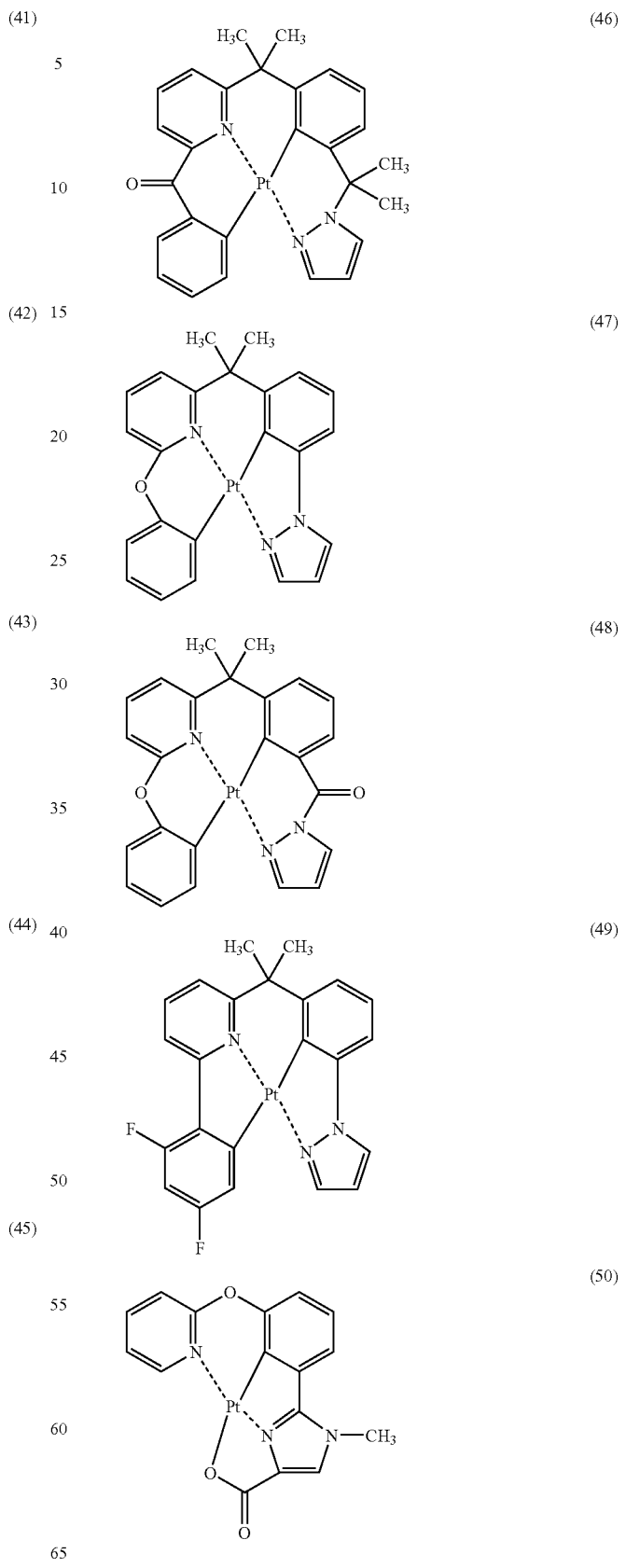

-continued
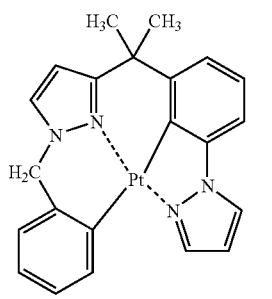 (51)
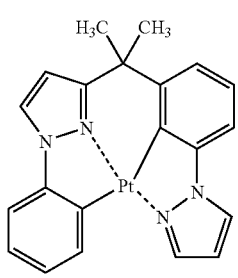 (52)
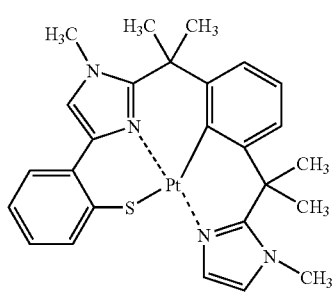 (53)
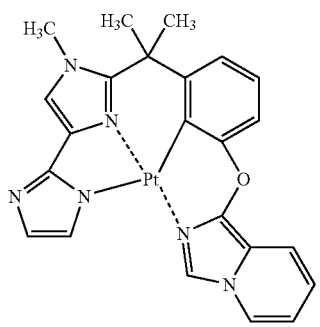 (54)
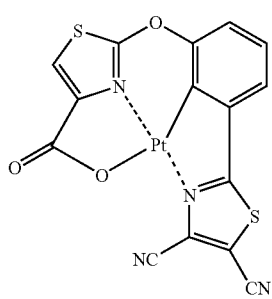 (55)
-continued
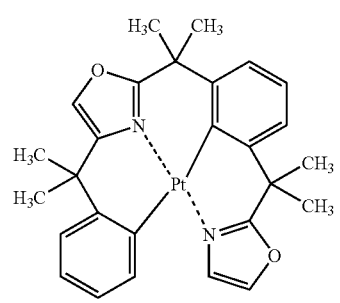 (56)
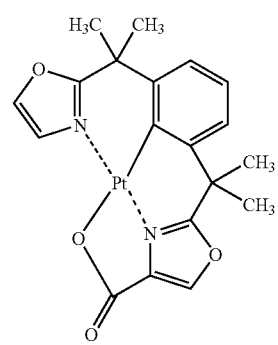 (57)
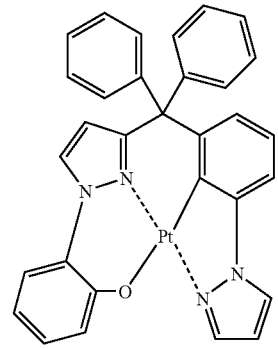 (58)
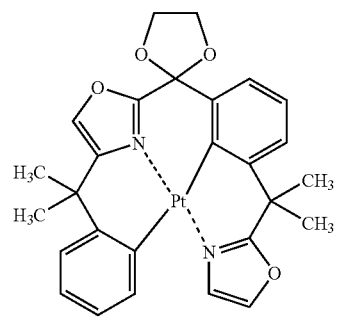 (59)

-continued (60)

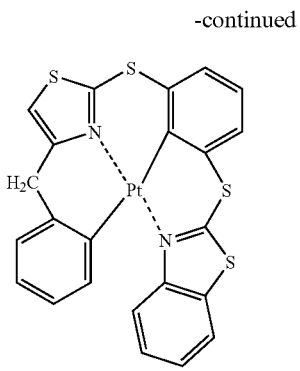

The compound represented by formula (I) can be synthesized by various known techniques. An exemplary method comprises leaving a compound containing a platinum ion and a ligand or dissociated body thereof at room temperature or under heating (a method using a mantle heater or a microwave oven is also effective, in addition to ordinary heating methods) in the presence or absence of a solvent (e.g., a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent and water) in the presence or absence of a base (e.g., various types of inorganic and organic bases, such as sodium methoxide, t-butoxy potassium, triethyl amine and potassium carbonate).

The reaction time for the synthesis of the compound represented by formula (I) according to the invention may be changed depending on the activity of the reaction, thus is not particularly limited. From the viewpoint of enhancement of the yield, the reaction time is preferably 1 minute to 5 days, more preferably 5 minutes to 3 days, and still more preferably 10 minutes to 24 hours.

The reaction temperature for the synthesis of the compound represented by formula (I) according to the invention may be changed depending on the activity of the reaction, thus is not particularly limited. From the viewpoint of enhancement of yield, the reaction temperature is preferably 0° C. to 300° C., more preferably 5° C. to 250° C., and still more preferably 10° C. to 200° C.

The compound represented by formula (I) according to the invention can be synthesized by adding a ligand to form a partial structure of the target complex. The amount of the ligand to be added is preferably 0.1 equivalent to 10 equivalents, more preferably 0.3 equivalent to 6 equivalents, and still more preferably 0.5 equivalent to 4 equivalents, based on the amount of the platinum compound.

The platinum compound may be a halide (e.g., platinum chloride or potassium chloroplatinate), a carboxylic salt (e.g., platinum acetate), a diketonate (e.g., platinum acetyl acetonate), a platinum compound containing an organic ligand (e.g., dichlorocyclooctadienyl platinum), or a hydrate of any of the above compounds.

Next, specific examples of the synthesis of exemplified compound (1) among compounds represented by formula (I) according to the invention will be described below. However, usable synthesis methods are not limited thereto.

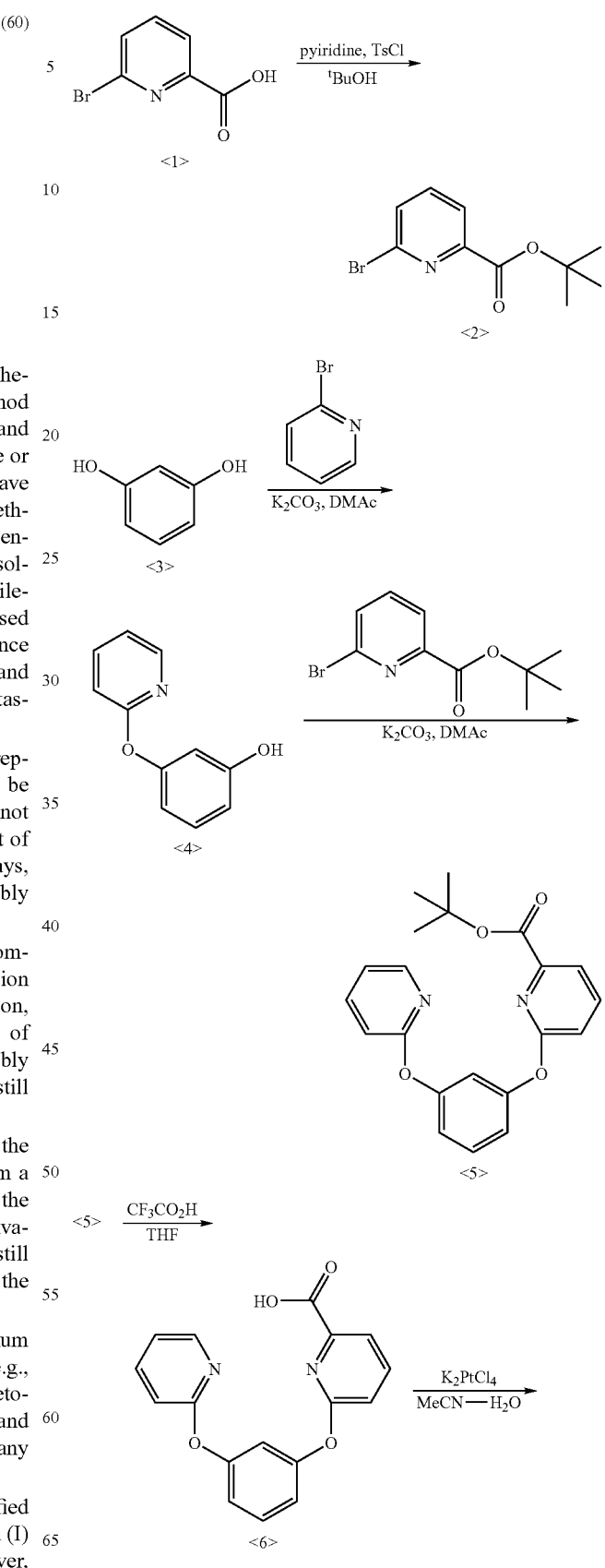

-continued

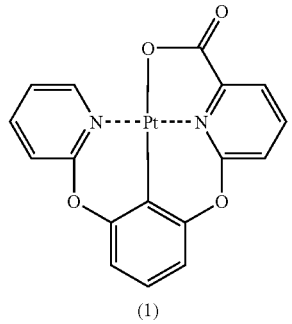

(1)

3.0 g (0.015 mol) of 6-bromopicolinic acid <1>, 30 g of t-butyl alcohol and 9.0 ml (0.045 mol) of pyridine were put in a 100-ml three-neck flask. While the resultant mixture was stirred in an ice-cooled condition, 5.0 g (0.026 mol) of p-toluene sulfonyl chloride was added thereto, and the resultant mixture was stirred in an ice-cooled condition for one hour. Thereafter, the temperature was gradually raised to room temperature. Water was added to the reaction mixture to precipitate a crude crystal, and the crude crystal was then separated by filtration. The thus-separated crude crystal was dissolved in ethyl acetate, and then dried by using magnesium sulfate anhydrous, and inorganic salts were removed by filtration. The resultant filtrate was condensed by a rotary evaporator, thereby producing a crystal. The obtained crystal was washed by being dispersed in hexane. As the result, 3.02 g of a compound <2> was obtained with a yield of 79%.

$^1$H-NMR (300 MHz, CDCl$_3$) δ=7.97 (dd, J=1.2, 6.8 Hz, 1H), 7.65 (t, J=8.0 Hz, 1H), 7.62 (dd, J=1.6, 7.6 Hz, 1H), 1.62 (s, 9H).

89 g (0.81 mol) of resorcinol <3>, 64.0 g (0.405 mol) of 2-bromopyridine, 168 ml of N,N-dimethyl acetamide and 168 g (1.22 mol) of potassium carbonate were put in a 500-ml three-neck flask, and then the resultant mixture was heated and stirred for 8 hours by a mechanical stirrer. Water and 10% diluted hydrochloric acid were added to the reaction mixture, so that the reaction mixture was neutralized. Thereafter, the aqueous layer was extracted with ethyl acetate three times. The organic layer thus collected was dried by using magnesium sulfate anhydrous, and subsequently condensed by a rotary evaporator under a reduced pressure. The resultant residue was purified by using a silica-gel-column chromatography, thereby producing 8.3 g of a compound <4> with a yield of 11%.

$^1$H-NMR (400 MHz, CDCl$_3$) δ=8.19 (dd, J=1.2, 4.8 Hz, 1H), 7.71 (ddd, J=2.0, 7.2, 8.0 Hz, 1H), 7.22 (t, J=8.0 Hz, 1H), 6.98-7.05 (m, 2H), 6.94 (br. d, J=8.4 Hz, 1H), 6.60-6.66 (m, 2H), 6.55 (br. t, J=2 Hz, 1H).

0.940 g (5.02 mmol) of the compound <4>, 1.08 g (5.51 mmol) of the compound <2>, 18 ml of N,N-dimethyl acetamide and 2.12 g (15.3 mmol) of potassium carbonate were put in a 100-ml three-neck flask, and then, the resultant mixture was stirred for 12 hours while maintained at 140° C. Then, water was added to the reaction mixture, and the aqueous layer was extracted with ethyl acetate three times. The organic layer thus collected was dried by using magnesium sulfate anhydrous, and inorganic salts were then removed by filtration. The resultant filtrate was condensed by using a rotary evaporator. The resultant residue was purified by using a silica-gel-column chromatography, thereby giving 0.25 g of a compound <5> with a yield of 14%.

$^1$H-NMR (400 MHz, CDCl$_3$) δ=8.21 (br. dd, J=1.6, 5.2 Hz, 1H), 7.77 (s, 1H), 7.76 (d, J=1.6 Hz, 1H), 7.69 (br. ddd, J=2.0, 7.2, 8.0 Hz, 1H), 7.40 (t, J=8.4 Hz, 1H), 6.97-7.10 (m, 5H), 6.94 (d, J=8.4 Hz, 1H), 1.59 (s, 9H).

136 mg (mmol) of the compound <5>, 5.0 ml of tetrahydrofuran and 0.2 ml of trifluoroacetic acid were put in a 100-ml three-neck flask, and then the resultant mixture was stirred for 8 hours while maintained at 80° C. The reaction mixture was condensed as it is in a reduced pressure, to give 109 mg of a pale yellow oily compound <6>. The obtained compound was immediately used in the subsequent process without being purified further.

$^1$H-NMR (400 MHz, CDCl$_3$) δ=8.42 (br. d, J=4.0 Hz, 1H), 8.06 (m, 1H), 7.98 (d, J=1.6 Hz, 1H), 7.97 (s, 1H), 7.54 (t, J=8.4 Hz, 1H), 7.33 (br. t, J=6.4 Hz, 1H), 7.25-7.30 (m, 1H), 7.05-7.18 (m, 3H), 7.02 (br. t, 2.4 Hz, 1H).

109 mg of the compound <6>, 147 mg (0.354 mmol) of potassium chloroplatinate, 30 ml of acetonitrile and 10 ml of water were put in a 100-ml three-neck flask, and then the resultant mixture was refluxed under heating for 15 hours in a flow of nitrogen. Water was added to the resultant mixture to generate a yellow crystal, and the crystal was separated by filtration. The crystal was then washed with acetonitrile and water. The resultant crude crystal was purified by using a silica-gel-column chromatography (solvent: chloroform), to give 19 mg of the exemplified compound (1) with a yield of 10% in 2 steps.

$^1$H-NMR (400 MHz, CDCl$_3$) δ=9.44 (dd, J=2.4, 6.0 Hz, 1H), 8.08 (dd, J=7.6, 8.8 Hz, 1H), 7.94 (dt, J=1.6, 8.0 Hz, 1H), 7.86 (dd, J=1.2, 6.0 Hz, 1H), 7.34 (dd, J=0.8, 8.4 Hz, 1H), 7.20-7.25 (m, 2H), 7.04-7.08 (m, 1H), 7.04 (dd, J=1.2, 8.0 Hz, 1H), 6.99 (dd, J=1.2, 6.8 Hz, 1H).

The exemplified compound (1) according to the invention showed luminance maximum in a dichloromethane solution at 480 nm at room temperature and 468 nm in a condition of being cooled by liquid nitrogen.

Next, the luminescent element containing the compound represented by formula (I) according to the invention is described.

The luminescent element of the invention is an element which utilizes a compound represented by formula (I) according to the invention. Ordinary luminescent systems, driving methods, and utilization manners are applicable to the luminescent element of the invention.

The light extraction efficiency of the luminescent element according to the invention can be enhanced by various known meathods. It is possible to enhance external quantum efficiency by improving the light extraction efficiency, for example, by modifying the surface of the substrate (for example, forming a fine concavo-convex pattern), by controlling refractive indices of the substrate, the ITO layer and the organic layer(s), or by regulating the thicknesses of the substrate, the ITO layer and the organic layer(s).

The external quantum efficiency of the luminescent element according to the invention is preferably 5% or more, more preferably 10% or more and still more preferably 13% or more.

The value of the external quantum efficiency may be the maximum value of the external quantum efficiency at the time the element is driven at 20° C. or may be a value of the external quantum efficiency at about 100 to about 300 cd/cm$^2$ (preferably 200 to 300 cd/m$^2$) at the time the element is driven at 20° C.

In the invention, the value of the external quantum efficiency refers to the maximum value of the external quantum efficiency at the time the element is driven at 20° C.

According to the invention, a direct-current constant voltage is applied to an EL element to cause light emission, using a source measure unit Model 2400 manufactured by Toyo Technica Corp. The luminance is measured by a luminance meter, BM-8, manufactured by Topkon, to determine the external quantum efficiency at 200 cd/m$^2$.

Specifically, the external quantum efficiency of the element can be calculated from measured luminance, luminescent spectrum and current density, and the relative luminosity curve. Namely, the number of inputted electrons can be determined based on the current density. Then, the luminance is converted into the number of emitted photons by performing an integral calculation using the luminescent spectrum and the relative luminosity curve (spectrum). Thus, the external quantum efficiency (%) can be calculated according to the following formula:

External quantum efficiency(%)=(number of emitted photons/number of electrons inputted into element)×100

The luminescent spectrum can be measured by a multi-channel analyzer, PMA-11, manufactured by Hamamatsu Photonics Co., Ltd.

The internal quantum efficiency of the luminescent element according to the invention is preferably 30% or more, more preferably 50% or more and, still more preferably, 70% or more. The internal quantum efficiency of the element can be calculated according to the following formula:

Internal quantum efficiency=External quantum efficiency/Light extraction efficiency In ordinary organic EL elements, the light extraction efficiency is about 20%. However, the light extraction efficiency can be enhanced to 20% or more by selecting appropriate shape of the substrate, the shape of the electrodes, the thickness of the organic layer(s), the thickness of inorganic layer(s), the refractive index of the organic layer(s), the refractive index of the inorganic layer(s), and the like.

The luminescent element according to the invention may also be of so-called "top emission type" in which the emitted light is taken out from the cathode side (such as described in JP-A Nos. 2003-208109, 2003-248441, 2003-257651 and 2003-282261, the disclosures of which are incorporated herein by reference).

The driving durability of the luminescent element according to the invention can be evaluated by the luminance half-life. The luminance half-life (the time the emission takes to diminish to half the initial luminance) can be measured by applying a direct-current constant voltage to the organic EL element to cause light emission (using, for example, a source measure unit Model 2400 manufactured by Toyo Technica Corp) and measuring the luminance by a luminance meter, BM-8, manufactured by Topkon.

It is preferable to utilize the compound represented by formula (I) according to the invention as a luminescent material. When the compound is utilized as a luminescent material, the luminescence may be ultraviolet emission or visible-light emission, and may be fluorescence emission or phosphorescence emission. A representative luminescent element is an organic EL (electroluminescence) element.

(Organic Electroluminescent Element)

In the following, the organic electroluminescent element according to the invention (hereinafter occasionally referred to also as "organic EL element") will be described in detail.

The luminescent element according to the invention comprises a cathode and an anode provided on a substrate, and at least one organic compound layer including an organic luminescent layer (hereinafter occasionally referred to also as "luminescent layer" for short) between these electrodes. From the viewpoint of characteristics of the luminescent element, at least one of the anode and the cathode is preferably transparent.

In a preferable example of the structure of the organic layers (organic compound layers), a hole transporting layer, a luminescent layer and an electron transporting layer are provided in this order from the anode side. A charge blocking layer or the like may be provided between the hole transporting layer and the luminescent layer, and/or between the luminescent layer and the electron transporting layer. A hole injecting layer may be provided between the anode and the hole transporting layer, and an electron injecting layer may be provided between the cathode and the electron transporting layer. Further, each layer may comprise two or more sub-layers.

(Substrate)

The substrate to be used in the invention is preferably a substrate that does not scatter or attenuate light emitted from an organic compound layer. Specific examples of the substrate include inorganic materials such as Yttria-stabilized Zirconia (YSZ) and glass; polyesters such as polyethylene terephthalate, polybutylene phthalate, and polyethylene naphthalate; and organic materials such as polystyrene, polycarbonate, polyether sulfone, polyallylate, polyimides, polycycloolefins, norbornene resin, and poly(chlorotrifluoroethylene).

When the substrate is made of glass, the glass is preferably non-alkali glass in order to reduce ions derived from the glass. When the substrate is made of soda lime glass, the substrate is preferably coated with a barrier coating such as silica. When an organic material is used, the material is preferably excellent in heat resistance, dimension stability, solvent resistance, electric insulation and processability.

The shape, structure, size and the like of a substrate are not particularly limited and can be selected as appropriate depending on the applications, purposes and the like of a luminescent element. In general, the substrate is preferably board-shaped. The structure of the substrate may be a single-layer structure or a laminated structure. The substrate may comprise only one member or may comprise two or more members.

The substrate may be colorless transparent or colored transparent, and is preferably colorless transparent in view of no scattering or attenuation of the light emitted from the luminescent layer.

A moisture penetration resistance layer (gas barrier layer) can be formed on the front surface or back surface of the substrate.

Materials for the moisture penetration resistance layer (gas barrier layer) that are suitably used include inorganic substances such as silicon nitrate and silicon oxide.

The moisture penetration resistance layer (gas barrier layer) can be formed by, for example, the high-frequency sputtering process or the like.

When a thermoplastic substrate is used, the substrate may be further comprise a hard coat layer or an undercoat layer as required.

<Anode>

The anode may usually serve as an electrode that supplies holes to the organic compound layer. The shape, structure, size and the like of the anode are not particularly limited and can be selected as appropriate from well known electrodes depending on the application and purpose of the luminescent element. As mentioned supra, the anode is usually a transparent anode.

Examples of materials suitable for the anode include metals, alloys, metal oxides, electric conductive organic compounds and mixtures thereof Specific examples the material of the anode include electric conductive metal oxides such as tin oxides doped with antimony or fluorine (ATO, FTO), tin oxide, zinc oxide, indium oxide, indium tin oxide (ITO), and indium zinc oxide (IZO); metals such as gold, silver, chromium, and nickel; mixtures or laminates of these metals and electric conductive metal oxides; electric conductive inorganic substances such as copper iodide and copper sulfate; electric conductive organic materials such as polyaniline, polythiophene, and polypyrrole; laminates and the like of these and ITO. Among them, the material of the anode is preferably an electric conductive metal oxide, and more preferably ITO from the viewpoint of productivity, high electric conductivity, transparency and the like.

An anode can be formed on the above-described substrate by a method appropriately selected, in consideration of its suitability to the materials constituting the above-described anode, from wet methods such as the printing method and the coating method, physical methods such as the vacuum deposition method, the sputtering method and the ion plating method, chemical methods such as CVD and the plasma CVD method, and the like. For instance, when ITO is selected as the material of the anode, the formation of the anode can be carried out according to the direct current or high-frequency sputtering method, the vacuum deposition method, the ion plating method or the like.

In the organic electroluminescent element of the invention, the position of the anode to be formed is not particularly limited and can be selected as necessary depending on the applications or purposes of the luminescent element. The anode may be formed on the entire surface of one surface of the substrate, or on a portion thereof.

The patterning for forming the anode may be carried out by chemical etching such as photolithography, or by physical etching such as by means of a laser, or by vacuum deposition or sputtering after placing a mask, or by the lift-off method or the printing method.

The thickness of the anode can be selected appropriately depending on the material constituting the above-described anode, and cannot be specified unconditionally. The thickness of the anode may be usually 10 nm to 50 µm, and is preferably 50 nm to 20 µm.

The electric resistance of the anode is preferably $10^3$ Ω/sq or less, and more preferably $10^2$ Ω/sq or less. When the anode is a transparent anode, the anode may be colorless transparent or colored transparent. For the extraction of light emission from the anode side, the transmittance is preferably 60% or more, and more preferably 70% or more.

Additionally, transparent anodes which can be applied to the present invention are described in detail in "*Tohmeidodenmaku No Shintenkai* (*Developments of Transparent Conductive Films*)" edited by Yutaka Sawada, published by CMC (1999), the disclosure of which is incorporated by reference herein. When a plastic substrate of low heat resistance is used, ITO or IZO may be employed, and a transparent anode film formed at a low temperature of 150° C. or less is preferable.

<Cathode>

The cathode may usually serve as an electrode that injects an electron to an organic compound layer. The shape, structure, size and the like are not particularly limited and can be selected as appropriate from well known electrodes depending on the application and purpose of a luminescent element.

Examples of the material of the cathode include metals, alloys, metal oxides, electric conductive compounds and mixtures thereof Specific examples include alkali metals (e.g., Li, Na, K, Cs and the like), alkali earth metals (e.g., Mg, Ca, and the like), gold, silver, lead, aluminum, sodium-potassium alloy, lithium-aluminum alloy, magnesium-silver alloy, indium, rare earth metals such as ytterbium, and the like. Only one cathode material may be used, or two or more cathode materials may be used from the viewpoint of compatibility between stability and electron injection properties.

Among the materials usable for the cathode, alkali metals and alkali earth metals are preferable in view of electron injection properties, and materials primarily made of aluminum are preferable in view of excellent shelf life.

The material primarily made of aluminum usable in the invention is aluminum alone, or an alloy of aluminum and a 0.01 to 10% by mass of an alkali metal or alkali earth metal or a mixture thereof (e.g., lithium-aluminum alloy, magnesium-aluminum alloy, and the like).

In addition, materials for the cathode are described in JP-A Nos. 2-15595 and 5-121172, the disclosures of which are incorporated by reference herein, and the materials described in these gazettes can also be applied to the invention.

Methods of forming the cathode are not particularly limited, and may be selected from well known methods. For instance, a cathode can be formed by an appropriate method selected, in consideration of its suitability to the materials constituting the above-described cathode, from wet methods such as the printing method and the coating method; physical methods such as the vacuum deposition method, the sputtering method and the ion plating method; chemical methods such as CVD and the plasma CVD method; and the like. For example, when a metal or the like is selected as the cathode material, the formation of the cathode may be conducted using only one cathode material, or may be conducted using two or more cathode materials. When two or more cathode materials are used, they may be deposited at the same time or one by one by the sputtering method or the like.

The patterning for forming the cathode may be carried out by chemical etching such as photolithography, or by physical etching such as by means of a laser, or by vacuum deposition or sputtering after placing a mask, or by the lift-off method or the printing method.

In the invention, the position of the cathode to be formed is not particularly limited. The cathode may be formed on the entire organic compound layer, or on a portion thereof.

Also, a dielectric layer with a thickness of 0.1 nm to 5 nm made of a fluoride or oxide of an alkali metal or alkali earth metal, or the like, may be provided between the cathode and the organic compound layer. This dielectric layer can be considered to be a kind of electron injecting layer. The dielectric layer can be formed by, for example, the vacuum deposition method, the sputtering method, the ion plating method or the like.

The thickness of the cathode can be selected appropriately depending on the material constituting the above-described cathode, and cannot be specified unconditionally. The thickness of the cathode may be normally 10 nm to 5 µm, and is preferably 50 nm to 1 µm.

The cathode may be transparent or opaque. A transparent cathode can be formed by a process that involves forming a thin film of the cathode material to a thickness of from 1 to 10 nm, and then depositing thereon a transparent electric-conductive material, such as ITO, IZO, or the like.

<Organic Layer>

The organic layer (hereinafter occasionally referred to also as "organic compound layer") according to the invention is described.

The organic electroluminescent element according to the invention comprises a pair of electrodes and at least one organic compound layer including a luminescent layer (hereinafter, referred to also as "organic luminescent layer") between the pair of electrodes. Examples of organic compound layers other than the organic luminescent layer include, as described above, a hole transporting layer, an electron transporting layer, a charge blocking layer, a hole injecting layer, an electron injecting layer and the like.

—Formation of Organic Compound Layer—

In the organic electroluminescent element according to the invention, each organic compound layer can be formed by any of a dry film-forming method (such as a vapor-deposition method or a sputtering method), a transfer method, a printing method or the like.

—Luminescent Layer (Organic Luminescent Layer)—

The luminescent layer is a layer having a function of emitting light by the recombination of a hole with an electron. The luminescent layer receives a hole from the anode, the hole injecting layer or the hole transporting layer upon application of an electric field, and receives an electron from the cathode, the electron injecting layer or the electron transporting layer.

The luminescent layer in the invention may comprise a luminescent material alone or may comprise a mixture of a host material and a luminescent material. The luminescent material may be a fluorescence-emitting material or a phosphorescence-emitting material. Only one luminescent material (dopant) may be used, or two or more luminescent materials (dopants) may be used. The host material is preferably a charge transporting material. Only one host material may be used, or two or more host materials may be used. For example, the luminescent layer may have a constitution in which a electron-transporting host material and a hole-transporting host material are mixed. Further, a non-luminescent material having no charge transporting property may be contained in the luminescent layer.

The luminescent layer may comprise only one layer or two or more layers. When there are two or more layers, they may emits lights of different colors.

Examples of fluorescent materials that can be used with the compound represented by formula (I) include a benzoxazole derivative, a benzimidazole derivative, a benzothiazole derivative, a styrylbenzene derivative, a polyphenyl derivative, a diphenylbutadiene derivative, a tetraphenylbutadiene derivative, a naphthalimide derivative, a coumarin derivative, a condensed aromatic compound, a perynone derivative, an oxadiazole derivative, an oxazine derivative, an aldazine derivative, a pyralidine derivative, a cyclopentadiene derivative, a bis-styrylanthracene derivative, a quinacridone derivative, a pyrrolopyridine derivative, a thiadiazolopyridine derivative, a cyclopentadiene derivative, a styrylamine derivative, a diketopyrrolopyrrole derivative, an aromatic dimetylidine compound, various metallic complexes represented by metallic complexes of 8-quinolinol derivatives or metallic complexes of pyrromethene derivatives, a polymer compound such as polythiophene, polyphenylene or polyphenylenevinylene, and an organic silane derivative.

As for the ligand in the complex, for example, the ligands described in the following documents are usable: G Wilkinson et al, Comprehensive Coordination Chemistry, Pergamon Press (1987), H. Yersin, Photochemistry and Photophysics of Coordination Compounds, Springer-Verlag (1987), and Akio Yamamoto, Organometallic Chemistry—Principles and Applications—, Shokabo Publishing Co. Ltd. (1982), the disclosures of which are incorporated herein by reference.

Preferred examples of the ligand include a halogen ligand (preferably, a chlorine ligand), a nitrogen-containing heterocyclic ligand (e.g., phenylpyridine, benzoquinone, quinolinol, bipyridyl or phenanthroline), a diketone ligand (e.g., acetylacetone), a carboxylic acid ligand (e.g., acetic acid ligand), a carbon monoxide ligand, an isonitrile ligand, and a cyano ligand. More preferred example is a nitrogen-containing heterocyclic ligand. The complex may contain one transition metal atom, or may be a multinuclear metal complex containing two or more transition metal atoms. The complex may contain different metal atoms within one complex.

Phosphorescent materials that can be used in combination with the compound represented by formula (I) may be selected, for example from the phosphorescent materials described in the following documents: U.S. Pat. Nos. 6,303,231 B1 and 6,097,147, WO Nos. 00/57676, 00/70655, 01/39234, 01/41512 A1, 02/02714 A2 and 02/15645 A1, JP-A No. 2001-247859, EP No. 1211257, JP-A Nos. 2002-226495, 2002-234894, 2001-247859, 2001-298470, 2002-173674, 2002-203678 and 2002-203679, Nature, vol. 395, p. 151 (1998), Applied Physics Letters, vol. 75, p. 4 (1999), Polymer Preprints, vol. 41, p. 770 (2000), Journal of American Chemical Society, vol. 123, p. 4304 (2001) and Applied Physics Letters, vol. 79, p. 2082 (1999), the disclosures of which are incorporated herein by reference.

When the compound represented by formula (I) is used as a luminescent material, the amount of the luminescence material in the luminescent layer is preferably 0.1 to 40% by mass, and more preferably 0.5 to 20% by mass.

Examples of host materials that can be contained in the luminescent layer include a material containing a carbazole skeleton, a material containing a diarylamine skeleton, a material containing a pyridine skeleton, a material containing a pyrazine skeleton, a material containing a triazine skeleton, a material containing an arylsilane skeleton, and the materials described below as examples of host materials in the hole injecting layer, the hole transporting layer, the electron injecting layer, and the electron transporting layer.

The amount of host material in the luminescent layer is preferably 50 to 99.9% by mass, and more preferably 70 to 99.8% by mass.

The ratio of luminescent material to host material in the luminescent layer is not particularly limited, and is preferably in the range of 0.1:99.9 to 40:60, more preferably in the range of 0.2:99.8 to 20:80, and particularly preferably in the range of 0.5:99.5 to 10:90, from the viewpoints of luminescent efficiency and durability.

The thickness of the luminescent layer is not particularly limited, and is usually in the range of 1 nm to 500 nm, preferably 5 nm to 200 nm, and still more preferably 10 nm to 100 nm.

—Hole Injecting Layer and Hole Transporting Layer—

The hole injecting layer and the hole transporting layer are layers having functions of receiving a hole from the anode or anode side and transporting the hole to the cathode side. The hole injecting layer and hole transporting layer each preferably comprise a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an organosilane derivative, or carbon.

From the viewpoint of reducing the driving voltage, the thickness of each of the hole injecting layer and the hole transporting layer is preferably 500 nm or less.

The thickness of the hole transporting layer is preferably 1 nm to 500 nm, more preferably 5 nm to 200 nm, and still more preferably 10 nm to 100 nm. Further, the thickness of the hole injecting layer is preferably 0.1 nm to 200 nm, more preferably 0.5 nm to 100 nm, and still more preferably 1 nm to 100 nm.

The hole injecting layer and the hole transporting layer each may be a single layer containing one or more of the above-described materials, or each may comprise plural layers having the same composition or different compositions.

—Electron Injecting Layer and Electron Transporting Layer—

The electron injecting layer and the electron transporting layer are layers having functions of receiving an electron from the cathode or cathode side and transporting the electron to the anode side. The electron injecting layer and electron transporting layer each preferably comprise a triazole derivative, an oxazole derivative, an oxadiazole derivative, an imidazole derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, an aromatic ring (such as naphthalene or perylene) having a tetracarboxylic acid anhydride, various metal complexes (e.g., a metal complex of a phthalocyanine derivative or a 8-quinolinol derivative, and a metal complex containing metal phthalocyanine, benzoxazole or benzothiazole as a ligand), or an organic silane derivative.

From the viewpoint of reducing driving voltage, thickness of each of the electron injecting layer and the electron transporting layer is preferably 500 nm or less.

The thickness of the electron transporting layer is preferably 1 nm to 500 nm, more preferably 5 nm to 200 nm, and still more preferably 10 nm to 100 nm. Further, the thickness of the electron injecting layer is preferably 0.1 nm to 200 nm, more preferably 0.2 nm to 100 nm, and still more preferably 0.5 nm to 50 nm.

The electron injecting layer and the electron transporting layer each may be a single layer containing one or more of the above-described materials, or each may comprise plural layers having the same composition or different compositions.

—Hole Blocking Layer—

The hole blocking layer is a layer having a function of blocking the hole transported from the anode side to the luminescent layer from passing through to the cathode side. According to the invention, a hole blocking layer may be provided as an organic compound layer which contacts the cathode side of the luminescent layer.

The organic compound of the hole blocking layer may be, for example, an aluminum complex such as BAlq, a triazole derivative, or a phenanthroline derivative such as BCP.

The thickness of the hole blocking layer is preferably 1 nm to 500 nm, more preferably 5 nm to 200 nm, and still more preferably 10 nm to 100 nm.

The hole blocking layer may be a single layer containing one or more of the above-described materials or may comprise a plural layers having the same composition or different compositions.

(Protective Layer)

In the invention, the whole organic EL element may be protected by a protective layer.

Any material may be contained in the protective layer insofar as it has the ability to prevent the intrusion of materials, such as water and oxygen, which promote the deterioration of the element, into the element.

Specific examples of the material of the protective layer include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$, and $TiO_2$; metal nitrates such as SiNx and SiNxOy; metal fluorides such as $MgF_2$, LiF, $AlF_3$ and $CaF_2$; polyethylene, polypropylene, polymethylmethacrylate, a polyimide, polyurea, polytetrafluoroethylene, polychlorotrifluoroethylene, polydichlorodifluoroethylene, and a copolymer of chlorotrifluoroethylene with dichlorodifluoroethylene; copolymers obtained by copolymerization of a monomer mixture including tetrafluoroethylene and at least one kind of comonomer; fluorine-containing copolymers having a ring structure on the copolymer backbone thereof; water absorptive materials having a water absorption of 1% or more; moisture-proof materials having a water absorption of 0.1% or less; and the like.

A process of forming the protective layer is not particularly limited. Examples of usable methods include a vacuum deposition method, a sputtering method, a reactive sputtering method, a MBE (molecular beam epitaxy) method, a cluster ion beam method, a ion plating method, a plasma polymerization method (the high-frequency excited ion plating method), a plasma CVD method, a laser CVD method, a thermal CVD method, a gas source CVD method, a coating method, a printing method, and a transfer method.

(Sealing)

Furthermore, in the organic electroluminescent element of the invention, the entire element may be sealed with a sealing container.

Also, the space between the sealing container and the luminescent element may be filled with a moisture absorbent or an inert liquid. The moisture absorbent is not particularly limited. Specific examples of the moisture absorbent include barium oxide, sodium oxide, potassium oxide, calcium oxide, sodium sulfate, calcium sulfate, magnesium sulfate, phosphorus pentaoxide, calcium chloride, magnesium chloride, copper chloride, cesium fluoride, niobium fluoride, calcium bromide, vanadium bromide, a molecular sieve, zeolite, magnesium oxide, and the like. An inert liquid is not particularly limited and examples thereof include paraffins, liquid paraffins, fluorine-based solvents such as perfluoroalkanes, perfluoroamines and perfluoroethers, chlorine-based solvents, and silicone oils.

In the organic electroluminescent element of the present invention, a DC (which, if desired, may contain an AC component) voltage (usually from 2 to 15 V) or a DC current is applied between the anode and the cathode, whereby light emission can be obtained.

The method for driving the organic electroluminescent element of the invention may be selected from the driving methods described, for example, in JP-A Nos. 2-148687, 6-301355, 5-29080, 7-134558, 8-234685, and 8-241047, Japanese Patent No. 2784615, and U.S. Pat. Nos. 5,828,429 and 6,023,308, the disclosure of which are incorporated herein by reference.

EXAMPLES

Hereinafter, the present invention is described in more detail with reference to Examples. However, Examples should not be construed as limiting the invention.

Comparative Example 1

A washed ITO substrate was placed in a vapor-deposition apparatus, and NPD shown below was vapor-deposited thereon to a thickness of 50 nm. CBP and a compound 1-1' (compound described in Journal of Organometallic Chemistry, Vol. 689, pp. 2888 to 2899 (2004)) shown below were vapor-deposited thereon in a mass-ratio of 10 to 1 to a thickness of 40 nm. Subsequently, BAlq was vapor-deposited thereon to a thickness of 10 nm and Alq was vapor-deposited further thereon to a thickness of 30 nm. A patterned mask (to give a luminescent area of 4 mm×5 mm) was placed on the obtained organic thin film, and lithium fluoride was vapor-deposited thereon to a thickness of 3 nm and aluminum was vapor-deposited further thereon to a thickness of 60 nm, whereby an organic EL element was obtained.

When a direct-current constant voltage (5 V) was applied to the organic EL element, luminescence was not detected.

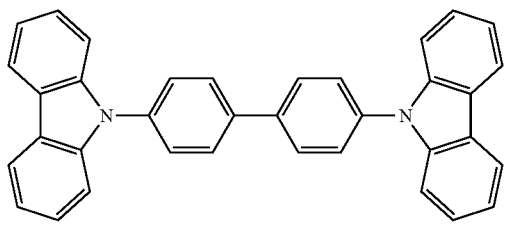

CBP

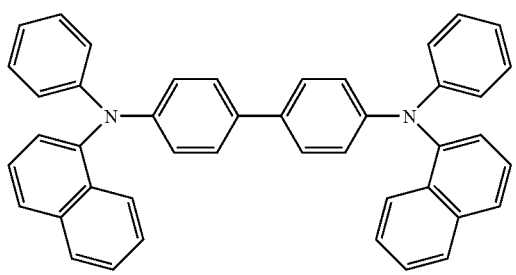

NPD

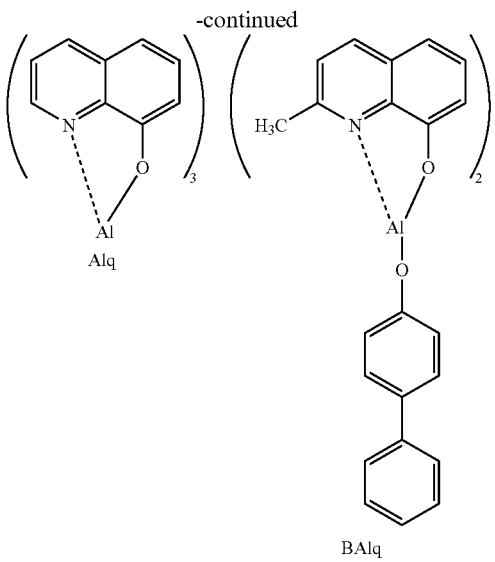

Alq

BAlq

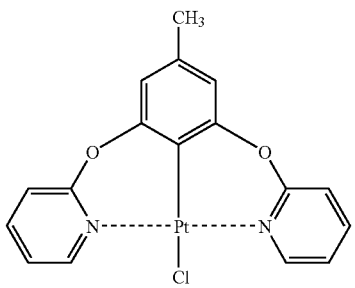

1-1'

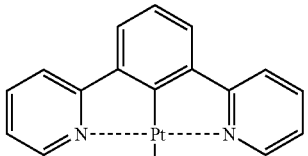

1-2'
(Compound described in WO2004/039914)

Comparative Example 2

An organic EL element was prepared in the same manner as in Comparative Example 1 except for using the compound 1-2' described in WO2004/039914 Pamphlet in place of the compound 1-1'.

When a direct-current constant voltage (5 V) was applied to the thus-prepared organic EL element, luminescence at 300 cd/m$^2$ was observed for 10 hours.

Example 1

An organic EL element was prepared in the same manner as in Comparative Example 1 except for using the compound (1) according to the invention in place of the compound 1-1' used in Comparative Example 1.

When a direct-current constant voltage (5 V) was applied to the thus-prepared organic EL element, luminescence was observed. When the element was allowed to emit light at 300 cd/m$^2$ for 10 hours, durability was found to be better than the electroluminescent element of Comparative Example 2.

In the same manner, when the compound represented by formula (1) according to the invention is used, an organic EL element having an excellent luminescence and high durability can be obtained. Further, the compound of the invention is capable of emitting phosphorescence of blue to green. Accordingly, an element capable of emitting luminescence of blue to green can be prepared by using the compound of the invention.

The luminescence element according to the invention can be advantageously utilized in the fields of display elements, displays, backlights, electrophotography, light sources for illumination, light sources for recording, light sources for exposure, light sources for reading, signs, sign boards, interior decorations and optical communications.

Further, the compound of the invention is also applicable to medical uses, fluorescent whitening agents, photographic materials, UV absorbing materials, laser dyes, materials for recording media, pigments for inkjet, dyes for color filters, color conversion filters, analytical applications, and the like.

What is claimed is:

1. An organic electroluminescent element comprising a pair of electrodes and at least one organic compound layer including a luminescent layer between the pair of electrodes, wherein at least one of the at least one organic compound layer comprises a compound represented by the following formula (IV):

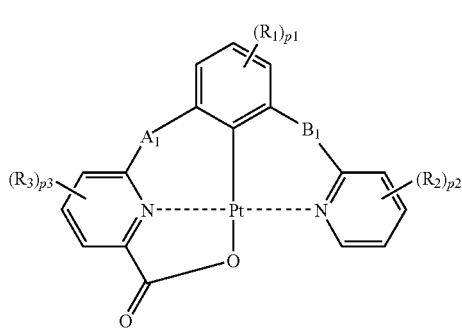

Formula (IV)

wherein in formula (IV), $A_1$ represents a linking group selected from the group consisting of —C($R_4$)($R_5$)—, —Si($R_6$)($R_7$)—, —N($R_{10}$)—, —O—, —S—, and —CO—; $B_1$ represents a linking group selected from the group consisting of —C($R_4$)($R_5$)—, —N($R_{10}$)—, —O—, —S—, and —CO—; $R_1$, $R_2$ and $R_3$ each independently represent a substituent; $R_4$, $R_5$, $R_6$, $R_7$ and $R_{10}$ each independently represent an alkyl group or an aryl group; $R_4$ and $R_5$ may be bonded to each other to form a ring; $R_6$ and $R_7$ may be bonded to each other to form a ring; and $p_1$, $p_2$ and $p_3$ each independently represent an integer of 0 to 3.

2. The organic electroluminescent element according to claim 1, wherein the compound of formula (IV) is represented by the following formula (VI):

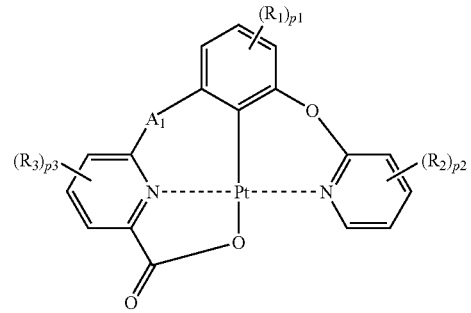

Formula (VI)

wherein in formula (VI), $R_1$, $R_2$ and $R_3$ each independently represent a substituent; $p_1$, $p_2$ and $p_3$ each independently represent an integer of 0 to 3; $A_1$ represents a linking group selected from the group consisting of —C($R_4$)($R_5$)—, —Si($R_6$)($R_7$)—, —N($R_{10}$)—, —O—, —S—, and —CO—; and $R_4$, $R_5$, $R_6$, $R_7$ and $R_{10}$ each independently represent an alkyl group or an aryl group; $R_4$ and $R_5$ may be bonded to each other to form a ring; $R_6$ and $R_7$ may be bonded to each other to form a ring.

3. The electroluminescent element according to claim 1, wherein the compound of formula (IV) is a polymer.

4. The electroluminescent element according to claim 3, wherein a weight-average molecular weight of the polymer is 1,000 to 5,000,000 in terms of polystyrene conversion.

5. The electroluminescent element according to claim 1, wherein the luminescent layer comprises the compound of formula (IV).

* * * * *